US 11,980,403 B2

(12) United States Patent
Rowe et al.

(10) Patent No.: US 11,980,403 B2
(45) Date of Patent: May 14, 2024

(54) IMPLANTABLE COMPRESSION SCREWS

(71) Applicant: GLOBUS MEDICAL, INC., Audubon, PA (US)

(72) Inventors: David J. Rowe, Parkesburg, PA (US); James A. Gault, Philadelphia, PA (US); David R. Jansen, Glenmoore, PA (US)

(73) Assignee: Globus Medical, Inc, Audubon, PA (US)

( * ) Notice: Subject to any disclaimer, the term of this patent is extended or adjusted under 35 U.S.C. 154(b) by 116 days.

(21) Appl. No.: 17/652,585

(22) Filed: Feb. 25, 2022

(65) Prior Publication Data

US 2022/0175430 A1 Jun. 9, 2022

Related U.S. Application Data

(63) Continuation of application No. 16/110,363, filed on Aug. 23, 2018, now Pat. No. 11,278,335, which is a continuation-in-part of application No. 15/132,368, filed on Apr. 19, 2016, now Pat. No. 10,531,905.

(51) Int. Cl.
| *A61B 17/86* | (2006.01) |
| *A61B 17/68* | (2006.01) |
| *A61B 17/88* | (2006.01) |

(52) U.S. Cl.
CPC .......... *A61B 17/863* (2013.01); *A61B 17/68* (2013.01); *A61B 17/8635* (2013.01); *A61B 17/8685* (2013.01); *A61B 17/888* (2013.01); *A61B 17/8888* (2013.01); *A61B 2017/681* (2013.01); *A61B 17/8605* (2013.01); *A61B 17/864* (2013.01); *A61B 2017/8655* (2013.01)

(58) Field of Classification Search
CPC ........ A61B 17/8685; A61B 2017/8655; A61B 2017/681
See application file for complete search history.

(56) References Cited

U.S. PATENT DOCUMENTS

| 4,175,555 | A | | 11/1979 | Herbert | |
| 4,432,358 | A | | 2/1984 | Fixel | |
| 4,858,601 | A | | 8/1989 | Glisson | |
| 5,217,462 | A | * | 6/1993 | Asnis | ................... A61B 17/888 606/301 |

(Continued)

FOREIGN PATENT DOCUMENTS

| CN | 103054642 A | 4/2013 |
| JP | 200433767 A | 2/2004 |
| WO | 2004069031 A2 | 8/2004 |

*Primary Examiner* — David W Bates

(57) ABSTRACT

A compression screw for applying compression at a bone joint. The compression screw includes an axial screw body extending from a distal end to a proximal end with the distal end including a series of bone engaging threads configured to be self-drilling and self-tapping and the proximal end including a head which defines a radially extending shoulder. At least one proximal rotary cutting structure is defined proximally of the bone engaging threads. The at least one proximal rotary cutting structure is configured to be self-drilling such that a proximal portion of the axial screw body cuts into and advances within a bone of the bone joint as the axial screw body is advanced. A method of inserting the compression screw is also provided.

15 Claims, 8 Drawing Sheets

(56) References Cited

U.S. PATENT DOCUMENTS

| | | | | |
|---|---|---|---|---|
| 5,498,265 | A | * | 3/1996 | Asnis ................ A61B 17/74 |
| | | | | 606/53 |
| 5,743,912 | A | | 4/1998 | Lahille et al. |
| 7,044,483 | B2 | | 5/2006 | Capanni |
| 7,794,483 | B2 | | 9/2010 | Capanni |
| 8,388,660 | B1 | * | 3/2013 | Abdou ............ A61B 17/8685 |
| | | | | 606/267 |
| 9,795,412 | B2 | * | 10/2017 | Sinha ............. A61B 17/8685 |
| 2003/0045881 | A1 | | 3/2003 | Barouk et al. |
| 2004/0068261 | A1 | | 4/2004 | Fourcault et al. |
| 2004/0210227 | A1 | * | 10/2004 | Trail ............... A61B 17/8635 |
| | | | | 606/328 |
| 2005/0143735 | A1 | * | 6/2005 | Kyle ................. A61B 17/742 |
| | | | | 606/60 |
| 2013/0338722 | A1 | * | 12/2013 | Yalizis ............ A61B 17/8625 |
| | | | | 606/312 |
| 2015/0150615 | A1 | * | 6/2015 | Anapliotis ....... A61B 17/8685 |
| | | | | 606/305 |
| 2015/0250515 | A1 | | 9/2015 | Terrill et al. |
| 2016/0287301 | A1 | | 10/2016 | Mehl et al. |
| 2018/0008317 | A1 | | 1/2018 | Sinha |

* cited by examiner

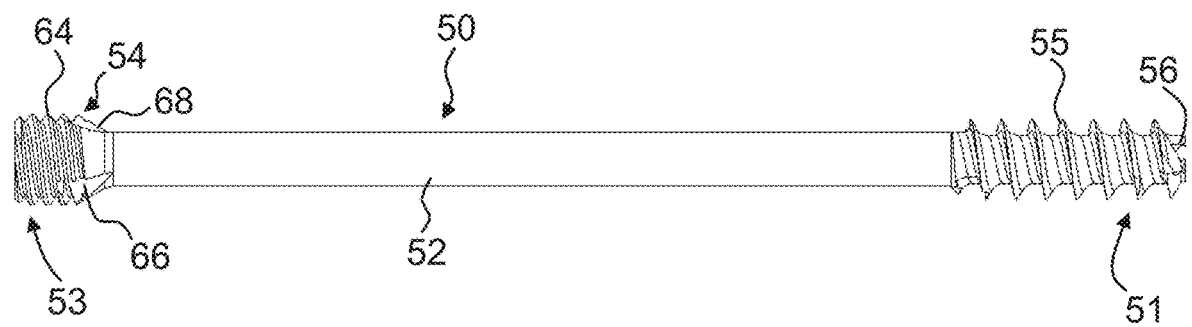
Fig. 14
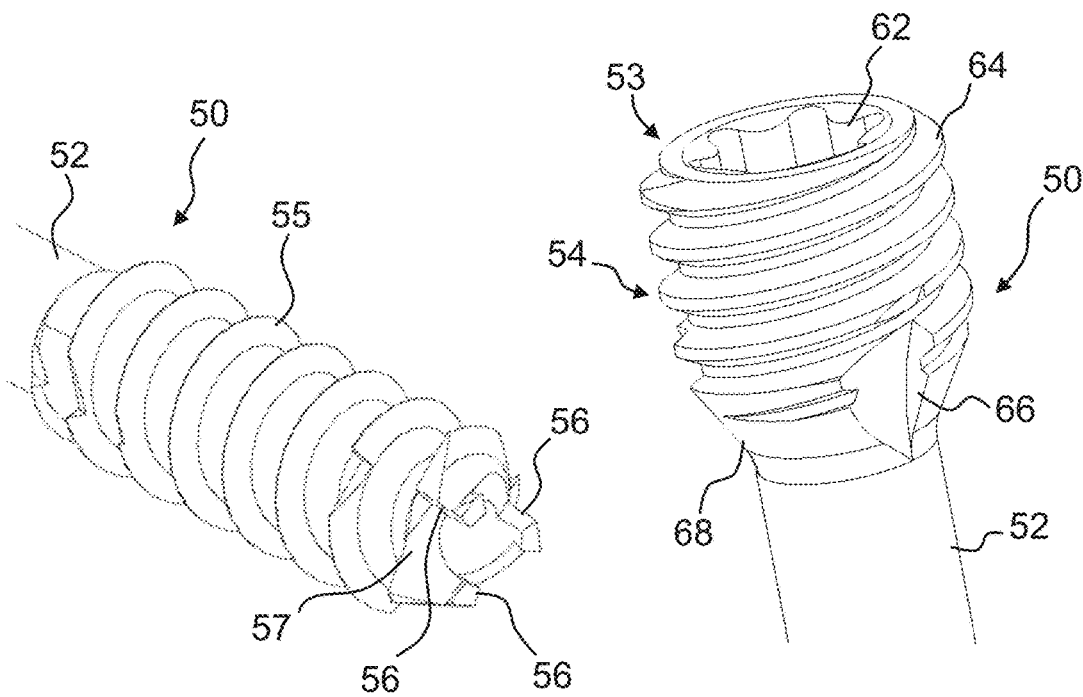
Fig. 15
Fig. 16

IMPLANTABLE COMPRESSION SCREWS

CROSS REFERENCE TO RELATED APPLICATIONS

This application is a continuation of U.S. patent application Ser. No. 16/110,363, filed Aug. 23, 2018, which is a continuation-in-part of U.S. patent application Ser. No. 15/132,368, filed Apr. 19, 2016, which is incorporated by reference herein in its entirety for all purposes.

FIELD OF THE INVENTION

The present disclosure relates to implantable screws. More particularly, the disclosure relates to implantable screws configured to provide compression upon a bone into which the screw is implanted.

BACKGROUND OF THE INVENTION

A broken bone must be carefully stabilized and supported until it is strong enough to handle the body's weight and movement. Until the last century, physicians relied on casts and splints to support and stabilize the bone from outside the body. The advent of sterile surgical procedures reduced the risk of infection, allowing doctors to internally set and stabilize fractured bones. During a surgical procedure to set a fracture, the bone fragments are first repositioned (reduced) into their normal alignment. They are held together with special implants, such as plates, screws, nails and wires.

Screws are used for internal fixation more often than any other type of implant. Although the screw is a simple device, there are different designs based on the type of fracture and how the screw will be used. Screws come in different sizes for use with bones of different sizes. Screws can be used alone to hold a fracture, as well as with plates, rods, or nails. After the bone heals, screws may be either left in place or removed.

In many instances, it is desired that the inserted screw provide compression at the bone joint or fracture line to reduce the incidence of nonunion (improper healing) and malunion (healing in improper position) of broken bones.

SUMMARY OF THE INVENTION

To meet this and other needs, devices, systems, and methods for fixating bone are provided. In particular, bone screws are provided that apply compression to bone fragments or bone portions (for example, fixation of fractures or fusion of joints), are self-tapping and/or self-drilling, minimize or prevent screw toggle and/or back-out, remove bone build-up (for example, from cutting flutes), and the like.

In at least one embodiment, a compression screw is provided for applying compression at a bone joint. The compression screw includes an axial screw body extending from a distal end to a proximal end with the distal end including a series of bone engaging threads configured to be self-drilling and self-tapping and the proximal end including a head which defines a radially extending shoulder. At least one proximal rotary cutting structure is defined proximally of the bone engaging threads. The at least one proximal rotary cutting structure is configured to be self-drilling such that a proximal portion of the axial screw body cuts into and advances within a bone of the bone joint as the axial screw body is advanced.

In at least one embodiment, the compression screw for applying compression at a bone joint includes a bone screw and a compression sleeve. The bone screw extends from a distal end to a proximal end with the bone screw distal end including a series of bone engaging threads configured to be self-drilling and self-tapping and the bone screw proximal end including a series of external threads. The compression sleeve has a tubular body extending from a distal end to a proximal end with the compression sleeve distal end defining a proximal rotary cutting structure and the compression sleeve proximal end including a head which defines a radially extending shoulder. The compression sleeve includes internal threads engaged with the bone screw external threads such that the compression sleeve and bone screw are threadably adjustable relative to one another. The proximal rotary cutting structure is configured to be self-drilling such that a portion of the compression sleeve cuts into and advances within a bone of the bone joint as the compression screw is advanced.

In at least one embodiment, a method of inserting a compression screw into a bone joint includes engaging the compression screw with a driver assembly, the driver assembly including a first driver and a second driver, the first and second drivers co-axial with one another and selectively rotatable together or independently of one another; rotating the first and second drivers simultaneously to advance the compression screw into the bone joint until the compression screw is at a first desired location; and rotating the first driver while maintaining the second driver stationary whereby at least a portion of the compression screw is further advanced into the bone joint such that a compressive force is applied to the bone joint.

According to yet another embodiment, a method for applying compression between a first bone portion and a second bone portion having a gap therebetween includes inserting a compression screw in the first bone portion and the second bone portion, the compression screw comprising an outer sleeve and an inner bone screw, the outer sleeve having a non-threaded head which defines a radially extending shoulder, and the inner bone screw being threadedly engaged with the outer sleeve, the compression screw being inserted into the first bone portion and the second bone portion as a single unit; and rotating the outer sleeve to move the inner bone screw toward the outer sleeve and reduce the gap between the first bone portion and the second bone portion. If desired, the entire compression screw may be removed by the outer sleeve.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 14 is a plan view of a compression screw according to another embodiment of the invention.

FIG. 15 is an expanded perspective view of the tip of the compression screw of FIG. 14.

FIG. 16 is an expanded perspective view of the head of the compression screw of FIG. 14.

DETAILED DESCRIPTION OF THE INVENTION

Figure 1:
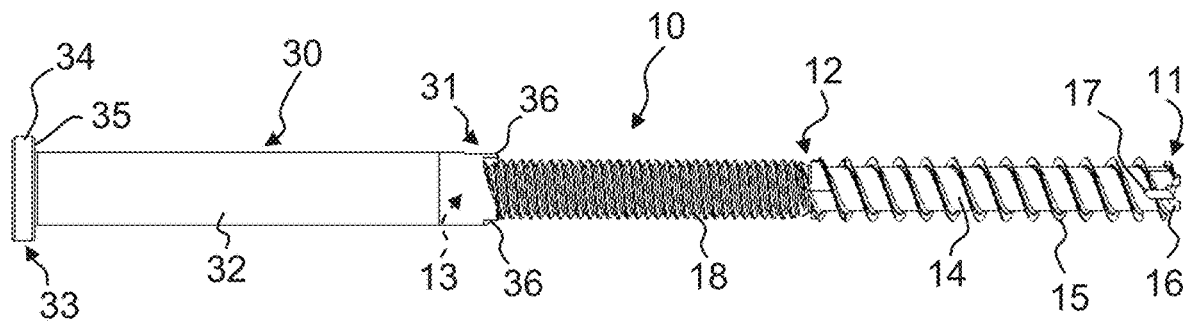
FIG. 1 is a plan view of a compression screw according to an embodiment of the invention.

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Devices, systems, and methods for fixating bone are provided. In particular, bone screws are provided that may apply compression to bone fragments or bone portions. This may be particularly effective, for example, in trauma applications for fixation of bone fractures and/or fusion of joints. The disclosed devices and methods may be used for repairing bones including, but not limited to, the femur, tibia, fibula, humerus, ulna, radius, metatarsals, phalanx, phalanges, ribs, spine, vertebrae, clavicle, and other bones. Any of the features described herein may be applied to standalone screws or screws that additionally include a compression sleeve.

Figure 2:
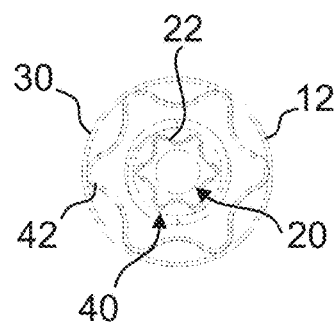
FIG. 2 is an end view of the compression screw of FIG. 1.
Figure 8:
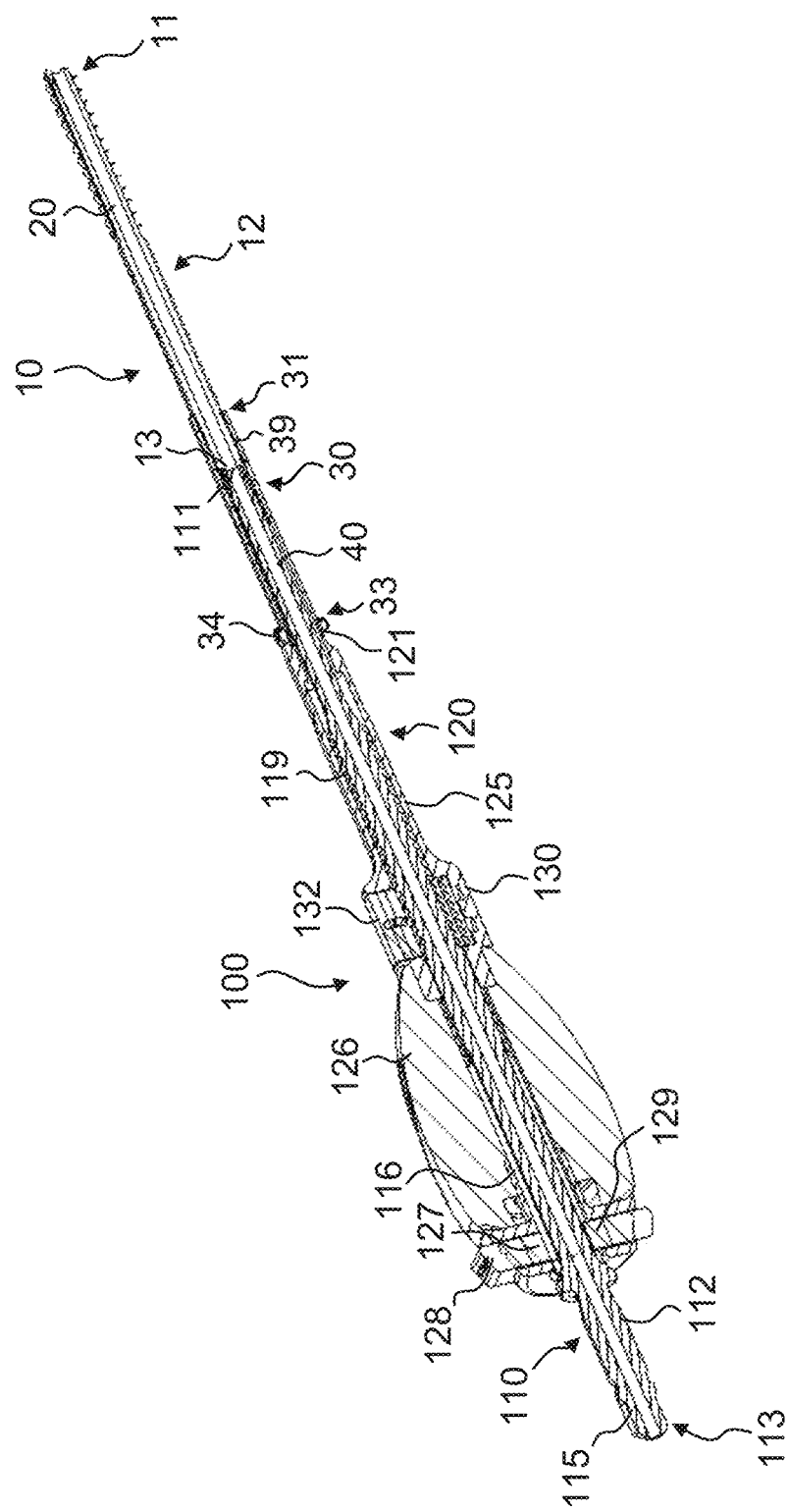
FIG. 8 is a cross-sectional view of the driver assembly of FIG. 7 engaged with the compression screw of FIG. 1.

Referring to FIGS. 1-2 and 8, a compression screw 10 in accordance with an embodiment will be described. The compression screw 10 generally comprises a bone screw 12 and a compression sleeve 30. The bone screw 12 and the compression sleeve 30 may be constructed from any biocompatible material including, but not limited to, stainless steel alloys, titanium, titanium based alloys, or polymeric materials.

The bone screw 12 includes a shaft 14 extending from a distal end 11 to a proximal end 13. Referring to FIGS. 2 and 8, in the illustrated embodiment, a cannula 20 extends from the distal end 11 to the proximal end 13 such that a guide wire may be used for positioning the compression screw 10. A drive feature 22 is defined in the proximal end 13 of the shaft 14 and is configured and dimensioned to be any shape that corresponds with the end of the driving instrument designed to engage the bone screw 12. As an example, in the illustrated embodiment, the drive feature 22 has a hexalobular configuration.

A series of bone engaging threads 15 extend radially from the shaft 14 at the distal end 11 and a series of sleeve engaging threads 18 extend radially from the shaft 14 at the proximal end 13. In the preferred embodiment, the bone engaging threads 15 are dual lead thread type and the sleeve engaging threads 18 are a standard machine thread. However, any type of thread for either thread series 15, 18 may be used to facilitate the function of the compression screw 10. The bone screw 12 preferably also includes at least one cutting flute 16 configured to cut into the bone as the bone screw 12 is rotated, defining a self-drilling and self-tapping tip. In a preferred embodiment, a slot 17 is associated with each cutting flute 16 to clear any chips, dust, or debris generated when the compression screw 10 is implanted into bone tissue.

The compression sleeve 30 includes a tubular body 32 extending from a distal end 31 to a proximal end 31 with an internal passage 40 therethrough. The compression sleeve 30 includes a series of internal threads 39 (see FIG. 8) configured to engage the sleeve engaging threads 18 of the bone screw 12 such that the bone screw 12 and the compression sleeve 30 are threadably adjustable to one another. The proximal end 33 of the compression sleeve 30 defines a radially extending head 34 which defines a shoulder 35 between the tubular body 32 and the head 34. A drive feature 42 is defined in the head 34 of the compression sleeve 30 and is configured and dimensioned to be any shape that corresponds with the end of the driving instrument designed to engage the compression sleeve 30. As an example, in the illustrated embodiment, the drive feature 42 has a hexalobular configuration.

As will be described in more detail hereinafter, during insertion of the implant, both drive features 22, 42 are engaged such that the compression screw 10 maintains its full length. After the tip of the bone screw 12 is at the desired depth, only the drive feature 42 in the compression sleeve 30 is actuated. Since the two components are connected via threads, actuation of only the compression sleeve 30 will act to move the compression sleeve 30 distally toward the tip of the bone screw 12, which shortens the length of the compression screw 10 and compresses the bone when the shoulder 35 of the compression sleeve 30 is on the near cortex.

To facilitate such shortening of the compression screw 10, the distal end 31 of the compression sleeve 30 is provided with one or more cutting flutes 36 configured to cut into the bone as the compression sleeve 30 is rotated. The cutting flutes 36 simplify the procedure by removing material without the necessity of drilling to the outer diameter of the compression sleeve tubular body 32. This also allows the compression screw 10 to be adjusted to any length without the need to predrill to a desired depth to accommodate the compression sleeve 30. In the present embodiment, the cutting flutes 36 define a proximal rotary cutting structure.

Figure 3:
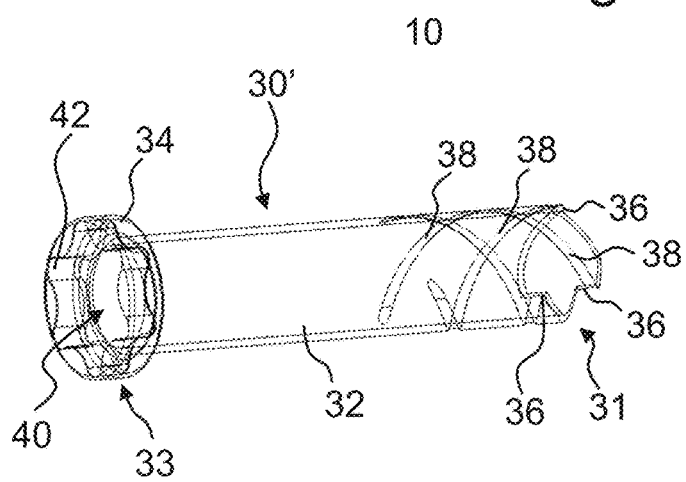
FIG. 3 is a perspective view of a compression sleeve in accordance with another exemplary embodiment.
Figure 4:
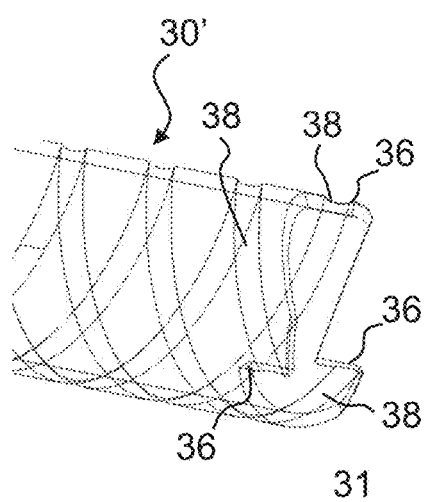
FIG. 4 is an expanded view of the cutting end of the compression sleeve of FIG. 3.

In the alternative embodiment of the compression sleeve 30' illustrated in FIGS. 3 and 4, a slot 38 is associated with each cutting flute 36, with each slot recessed into the surface of the tubular body 32 and configured to guide the aforementioned cut bone into the slots 38. The mechanism of action for this technology relies on first the cutting flutes 36 to remove material from the substrate that it is being inserted into. This material then follows through the path of the slots 38 by one of two mechanisms: (1) path of least resistance (the material has nowhere else to go) or (2) the trajectory of the slots 38 roughly follows the pitch of the cutting flutes 36 as it is advanced into the bone, and thus the cutaway material stays close to its original position as the screw advances axially via the screw's helix.

The slots 38 serve two functions: (1) the cut bone that follows the slots 38 acts to enhance the fit between the native bone and the component being inserted into the bone and (2) allows for bony ingrowth to prevent dislodging of the compression screw 10. The cutting flutes 36 act to remove bone and guide said removed bone into the slots 38. This is in effect a self-grafting feature of the compression sleeve 30 which enhances purchase. Surgeons will sometimes remove bone and pack it back into the implant to enhance purchase, however, this configuration on the compression sleeve 30 does that for them. Enhanced purchase acts to prevent screw toggle and screw axial motion. Even if the slots 38 are not filled with bone, they can act to prevent both screw toggle and screw axial motion by providing a surface to catch on the native bone. Additionally, the slots 38 provide a surface for bony ingrowth which can also prevent screw toggle and screw axial motion.

Figure 5:
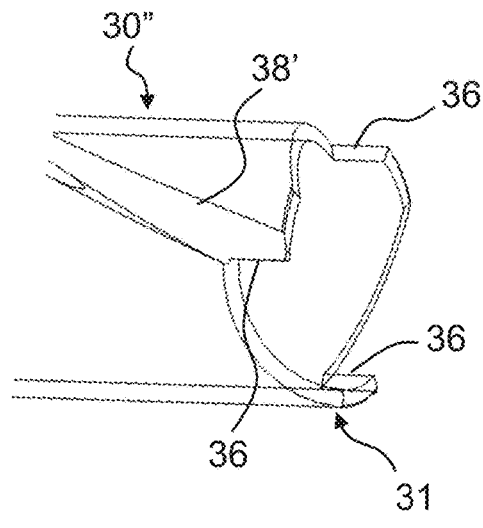
FIG. 5 is an expanded view of the cutting end of a compression sleeve in accordance with another exemplary embodiment.
Figure 6:
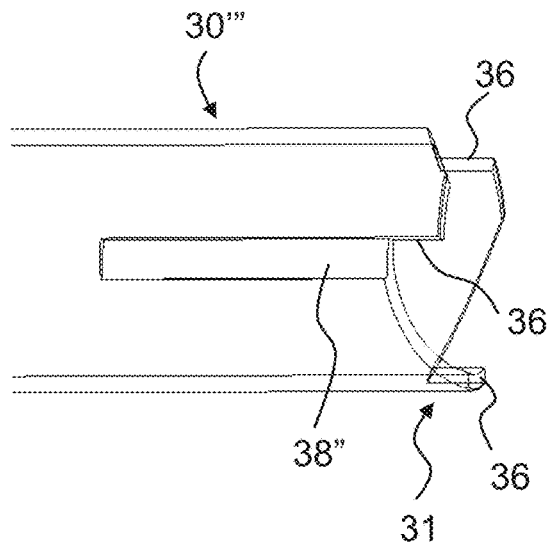
FIG. 6 is an expanded view of the cutting end of a compression sleeve in accordance with yet another exemplary embodiment.

While the trajectory of the slots 38 is shown in the embodiment of FIGS. 3 and 4 to roughly follow the pitch of the cutting flutes 36, the slots may have other configurations. For example, in the compression sleeve 30" illustrated in FIG. 5, the slot 38' has a steeper trajectory than the pitch of the cutting flutes. FIG. 6 illustrates another embodiment of the compression sleeve 30''' wherein the slot 38" has an even steeper trajectory, being substantially parallel to the axis of the compression sleeve 30'''. In addition to having different trajectories, the slots 38, 38', 38" may have different pitches resulting in the slots being spaced closer together or further apart. Additionally, the slots 38, 38', 38" may have different configurations, for example, semi-circular, semi-oval, v-shaped, square, rectangular or the like. Furthermore, while the combination of cutting flutes 36 and slots 38, 38', 38" are illustrated in conjunction with the compression sleeve 30, it is recognized that such can be applied to a surface of any type of component that is being inserted into bone.

Figure 7:
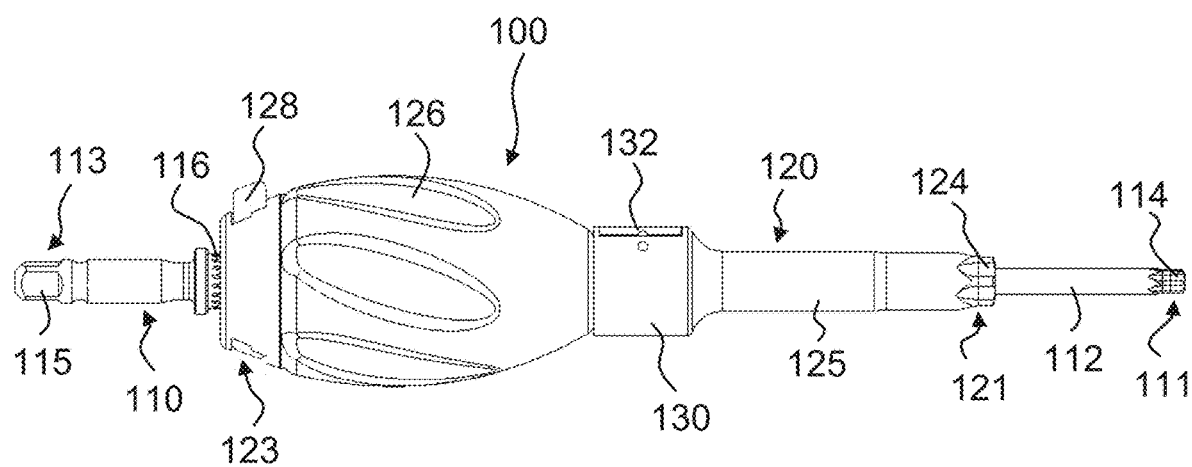
FIG. 7 is a plan view of an exemplary driver assembly configured for implantation of the compression screw of FIG. 1.

Having generally described the compression screw 10, an exemplary driver assembly 100 for inserting the compression screw 10 and an exemplary method of insertion will be described with reference to FIGS. 7 and 8.

The driver assembly 100 has a bone screw driver 110 and a compression sleeve driver 120. The bone screw driver 110 includes a driver shaft 112 extending from a distal end 111 to a proximal end 113. A driver tip 114 is defined on the distal end 111 of the driver shaft 112 and is configured to engage the driver feature 22 of the bone screw 12. A connection key 115 is defined on the proximal end 113 of the driver shaft 112 and is configured to facilitate connection of the bone screw driver 110 to a manual or powered rotation device or a locking device which prevents rotation (not shown). A series of axial splines 116 extend radially from the driver shaft 112 and are configured to be selectively engaged by a connector switch 128 of the compression sleeve driver 120, as will be described in more detail hereinafter. A series of external threads 119 extend from the driver shaft 112 distally of the splines 116. The external threads 119 are configured to be selectively engaged by a thread engagement member 132 of the compression sleeve driver 120, as will be described in more detail hereinafter.

The compression sleeve driver 120 extends from a distal end 121 to a proximal end 123. The proximal end 121 is defined by a tubular body 125 with a driver tip 124 at the distal most end and an outward housing 130 proximally therefrom. The driver tip 124 is configured to engage the driver feature 42 of the compression sleeve 30. The housing 130 defines a radial chamber in which the thread engagement member 132 is radially moveable. Upon depression of the thread engagement member 132, internal threads thereof engage the external threads 119 of the driver shaft 112 such that the driver shaft 112 is caused to move axially with the compression sleeve driver 120 when they are rotated together as will be described.

A handle member 126 extends proximally from the housing 130 to the proximal end 123. The connector switch 128 extends transversely through the handle member 126 and is moveable between a non-engaged position (see FIG. 8) and an engaged position (see FIG. 13). In the non-engaged position, an open area 129 of the connector switch 128 aligns with the splines 116 such that the switch 128 is not engaged with the splines 116 and the compression sleeve driver 120 rotates independent of the bone screw driver 110. In the engaged position, a contact portion 127 of the connector switch 128 engages the splines 116 such that rotation of the compression sleeve driver 120 causes simultaneous rotation of the bone screw driver 110.

To insert the compression screw 10, the driver assembly 100 is positioned such that the driver tip 114 of the shaft 112 engages with the drive feature 22 of the bone screw 12 and the driver tip 124 of the tubular body 125 engages with the drive feature 42 of the compression sleeve 30, as shown in FIG. 8. During initial insertion, the connector switch 128 is moved to the engaged position such that the bone screw driver 110 and the compression sleeve driver 120 rotate together. The driver assembly 100 is rotated with both drivers 110, 120 rotating and thus the compression screw 10 is advanced as a single unit until the distal end 11 of the bone screw 12 is at a desired location. The thread engagement member 132 may be depressed during such rotation to ensure that the shaft 112 advances axially during the simultaneous rotation. If the distal end 31 of the compression sleeve 30 contacts bone as the compression screw 10 is advanced, the proximal rotary cutting structure, i.e. the cutting flutes 36, cut into the bone and the compression screw 10 is free to continue to advance as a single unit.

After the distal end 11 of the bone screw 12 has landed at the desired location, compression may be achieved by advancing the compression sleeve 30 while the bone screw 12 remains stationary. The bone screw 12 remains stationary by holding the bone screw driver 110 stationary, for example, by attaching a locking device to the connection key 115, and by disengaging the connector switch 128. With the connector switch 128 moved to the disengaged position, the compression sleeve driver 120 rotates freely about the bone screw driver 110. Rotation of the compression sleeve driver 120 causes the compression sleeve 30 to advance. Since the bone screw 12 is stationary as the compression sleeve driver 120 advances the compression sleeve 30, the compression screw 10 shortens in length and the shoulder 35 thus applies compression. Again, the cutting flutes 36 on the compression sleeve distal end 31 allow the compression sleeve 30 to cut into and advance into the bone.

Figure 9:
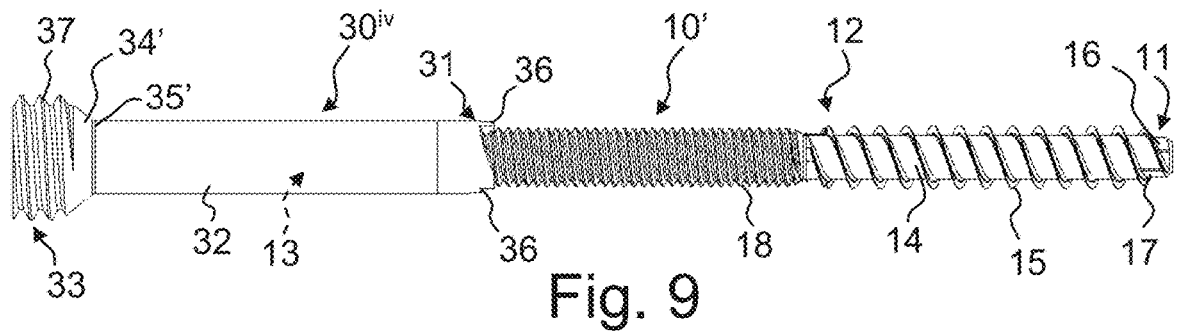
FIG. 9 is a plan view of a compression screw according to another embodiment of the invention.
Figure 10:
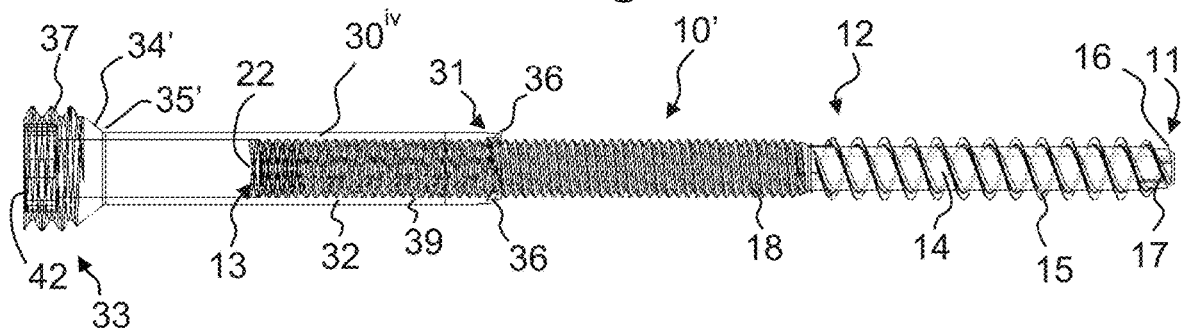
FIG. 10 is a plan view similar to FIG. 9 with the compression sleeve shown transparently.

Referring to FIGS. 9-10, a compression screw 10' in accordance with another exemplary embodiment will be described. The compression screw 10' is substantially the same as the previous embodiment except with the addition of a self-countersinking head 34' on the compression sleeve 30'. The self-countersinking head 34' has a tapered shoulder 35' and a series of external threads 37. The threads 37 are configured to be self-drilling and self-tapping. The self-countersinking head 34' is advantageous in that the head does not protrude from the near cortex, which minimizes soft-tissue irritation and can reduce the reoperation rate. In the present embodiment, the cutting flutes 36 and the threads 37 each define a proximal rotary cutting structure. In all other aspects, the compression screw 10' is the same as the previously described compression screw 10.

Figure 11:
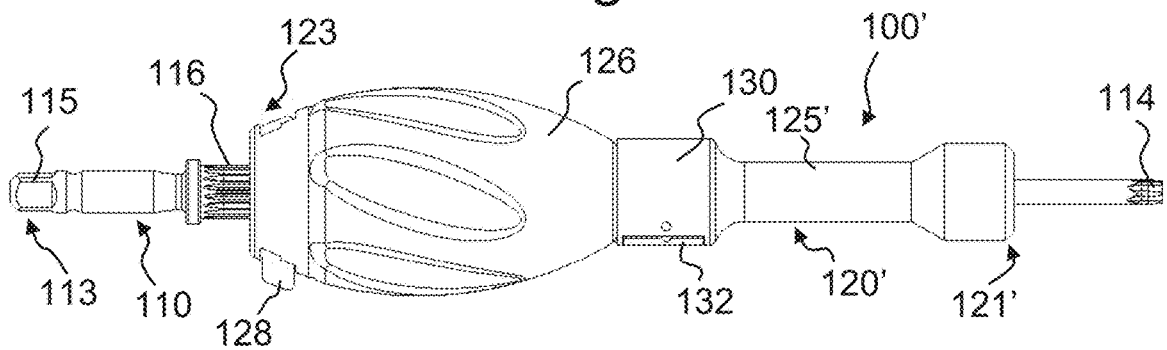
FIG. 11 is a plan view of an exemplary driver assembly configured for implantation of the compression screw of FIG. 9.
Figure 12:
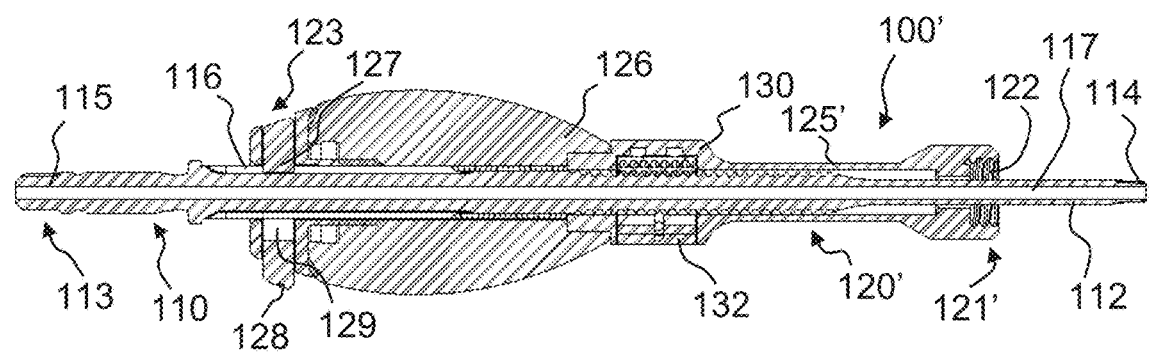
FIG. 12 is a cross-sectional view of the driver assembly of FIG. 11.
Figure 13:
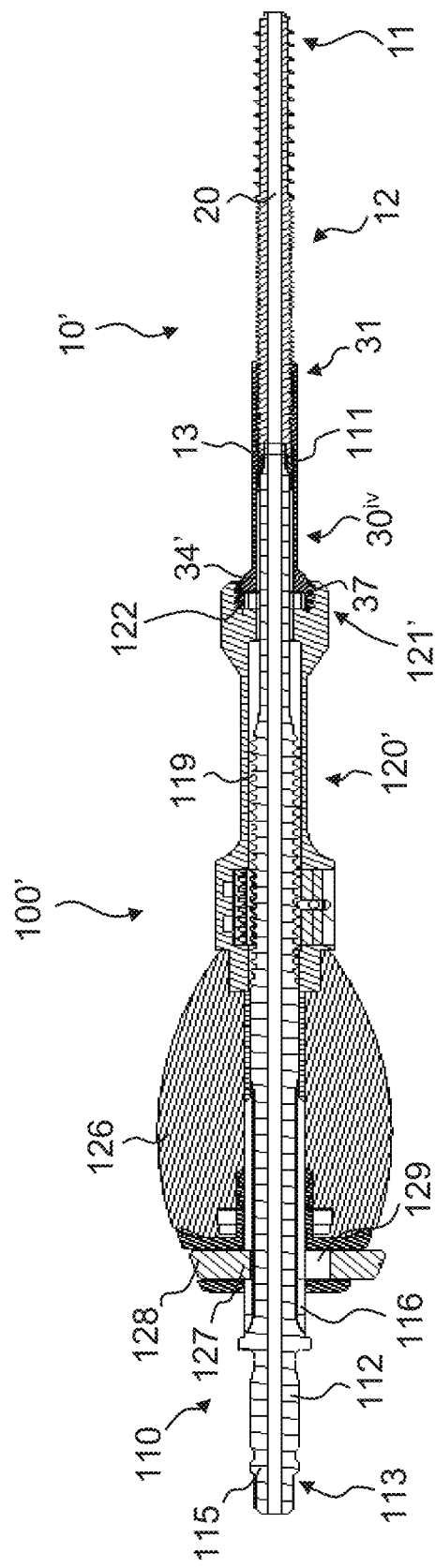
FIG. 13 is a cross-sectional view of the driver assembly of FIG. 11 engaged with the compression screw of FIG. 9.

Referring to FIGS. 11-13, a driver assembly 100' and method for inserting the compression screw 10' will be described. The driver assembly 100' is substantially the same as in the previous embodiment except for the distal end 121' of tubular body 125' of the compression sleeve driver 120'. Instead of a driver tip, the distal end 121' defines an internally threaded chamber 122 which threadably engages the threads 137 of the self-countersinking head 34'.

To insert the compression screw 10', the driver assembly 100' is positioned such that the driver tip 114 of the shaft 112 engages with the drive feature 22 of the bone screw 12 and the threads 137 of the self-countersinking head 34' are threadably received in the threaded chamber 122 of the compression sleeve driver 120', as shown in FIG. 13. During initial insertion, the connector switch 128 is moved to the engaged position such that the bone screw driver 110 and the compression sleeve driver 120' rotate together. The driver assembly 100' is rotated with both drivers 110, 120' rotating and thus the compression screw 10' is advanced as a single unit until the distal end 11 of the bone screw 12 is at a desired location. The thread engagement member 132 may be depressed during such rotation to ensure that the shaft 112 advances axially during the simultaneous rotation. If the distal end 31 of the compression sleeve $30^{iv}$ contacts bone as the compression screw 10' is advanced, the cutting flutes 36 cut into the bone and the compression screw 10' is free to continue to advance as a single unit.

After the distal end 11 of the bone screw 12 has landed at the desired location, compression may be achieved by advancing the compression sleeve $30^{iv}$ while the bone screw 12 remains stationary. The bone screw 12 remains stationary by holding the bone screw driver 110 stationary, for example, by attaching a locking device to the connection key 115, and by disengaging the connector switch 128. With the connector switch 128 moved to the disengaged position, the compression sleeve driver 120' rotates freely about the bone screw driver 110. Rotation of the compression sleeve driver 120' causes the compression sleeve $30^{iv}$ to advance. Since the bone screw 12 is stationary as the compression sleeve driver 120' advances the compression sleeve $30^{iv}$, the compression screw 10' shortens in length and the shoulder 35' and distal end 121' of the compression sleeve driver 120' thus apply compression. Again, the cutting flutes 36 on the compression sleeve distal end 31 allow the compression sleeve 30 to cut into and advance into the bone.

After the desired amount of compression has been reached, the head 34' may be countersunk. Countersinking is done by a third driver component (not shown) that mates with the compression sleeve driver feature 42. For example, the driver assembly 100 may be exchanged for the driver assembly 100' such that the driver tip 124 can be used to rotate the compression sleeve $30^{iv}$ while the bone screw 12 is maintained stationary. As the compression sleeve $30^{iv}$ advances over the bone screw 12, the threads 37 cut into the bone and advance the head 34' into a countersunk position within the bone.

Referring to FIGS. 14-16, a compression screw 50 in accordance with another embodiment will be described. The compression screw 50 includes a shaft 52 extending from a distal end 51 to a proximal end 53. A series of bone engaging threads 55 extend radially from the shaft 52 at the distal end 51. In the preferred embodiment, the bone engaging threads 55 are dual lead thread type, however, any type of thread may be used to facilitate the function of the compression screw 50. The distal end 51 preferably also includes at least one cutting flute 56 configured to cut into the bone as the compression screw 12 is rotated, defining a self-drilling and self-tapping tip. In a preferred embodiment, a slot 57 is associated with each cutting flute 56 to clear any chips, dust, or debris generated when the compression screw 50 is implanted into bone tissue.

The proximal end 53 of the shaft 52 includes a self-countersinking head 54. The self-countersinking head 54 has a tapered shoulder 68 and a series of external threads 64. The threads 64 may include one or more cutting flutes 66 such that the threads 64 are self-drilling and self-tapping. In the present embodiment, the threads 64 define a proximal rotary cutting structure. A drive feature 62 is defined in the proximal end 53 of the shaft 52 and is configured and dimensioned to be any shape that corresponds with the end of the driving instrument designed to engage the compression screw 50. As an example, in the illustrated embodiment, the drive feature 62 has a hexalobular configuration.

The shaft 52 between the bone engaging threads 55 and the head 54 is preferably free of threads. With this configuration, a difference in pitch between the bone engaging threads 55 and the threads 64 of the head 54 can provide additional compression control as the compression screw 50 is inserted. That is, if the pitch of the bone engaging threads 55 is larger than the pitch of the threads 64 of the head 54, and the fracture or joint line lies somewhere in the shaft 52 section of the screw 50, this configuration will provide compression between the two bones as the distal end 51 tries to advance faster than the head 54 of the screw 50.

Figure 17:
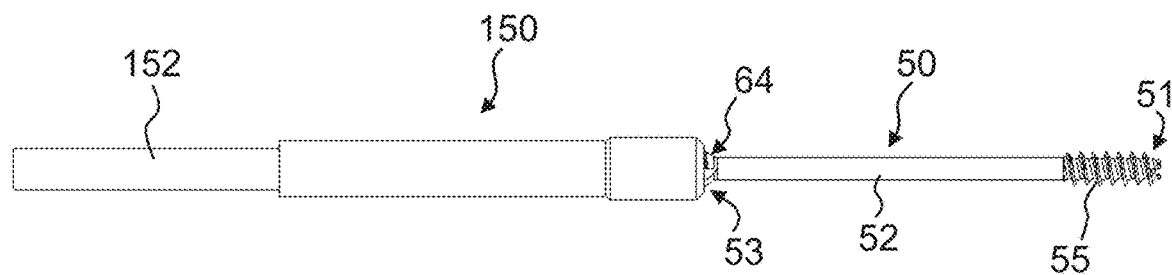
FIG. 17 is a plan view of an exemplary driver assembly engaging the compression screw of FIG. 14.
Figure 18:
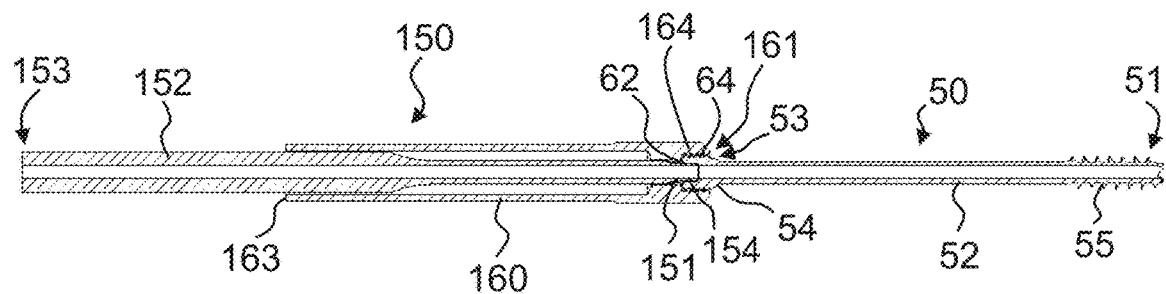
FIG. 18 is a cross-sectional view of the driver assembly of FIG. 17 engaged with the compression screw of FIG. 14.

Referring to FIGS. 17 and 18, a driver assembly 150 which allows the surgeon to further control how much compression is achieved will be described. The driver assembly 150 includes an inner driver member 152 and an outer driver member 160. The inner driver member 152 extends from a distal end 151 to a proximal end 153. A driver tip 154 is defined on the distal end 151 and is configured to engage the driver feature 62 of the compression screw 50.

The outer driver member 160 includes a tubular body extending from a distal end 161 to a proximal end 163. The distal end 161 defines a threaded chamber 164 configured to threadably receive the threads 64 of the compression screw head 54.

To insert the compression screw 50, the driver assembly 150 is positioned with the driver tip 154 engaged with the driver feature 62 and the threads 64 of the head 54 threadably received in the threaded chamber 164. The inner and outer driver members 152, 160 are rotated such that the compression screw 50 is advanced. As the compression screw 50 advances, the distal end 161 of the outer driver member 160 will hit the near cortex and compress the fracture line as the screw 50 is continued to be inserted.

After the desired amount of compression has been reached, the inner driver member 152 is rotated, independent of the outer driver member 160, such that the compression screw 50 continues to advance with the outer driver member distal end 161 maintaining the compression. As the compression screw 50 advances, the threads 64 of the head 54 will enter the bone and begin to countersink the head 54. As the head 54 advances and countersinks, it simultaneously threads out of the threaded chamber 164. As explained before, the pitch of the bone engaging threads 55 and the threads 64 of the head 54 may be configured such that countersinking of the head 54 causes additional compression.

Figure 19:
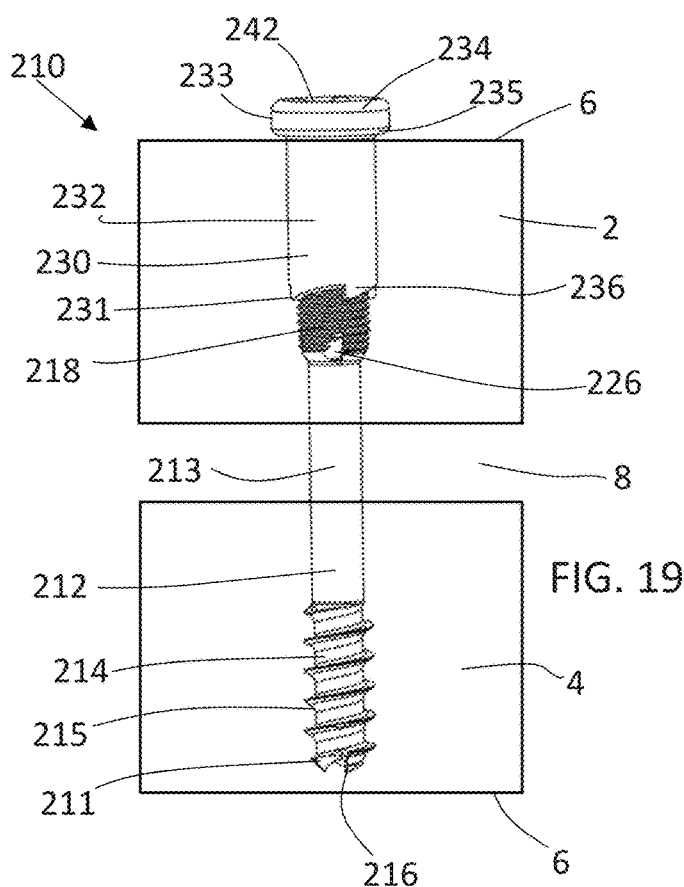
FIG. 19 is a plan view of an alternative compression screw according to another embodiment.
Figure 20:
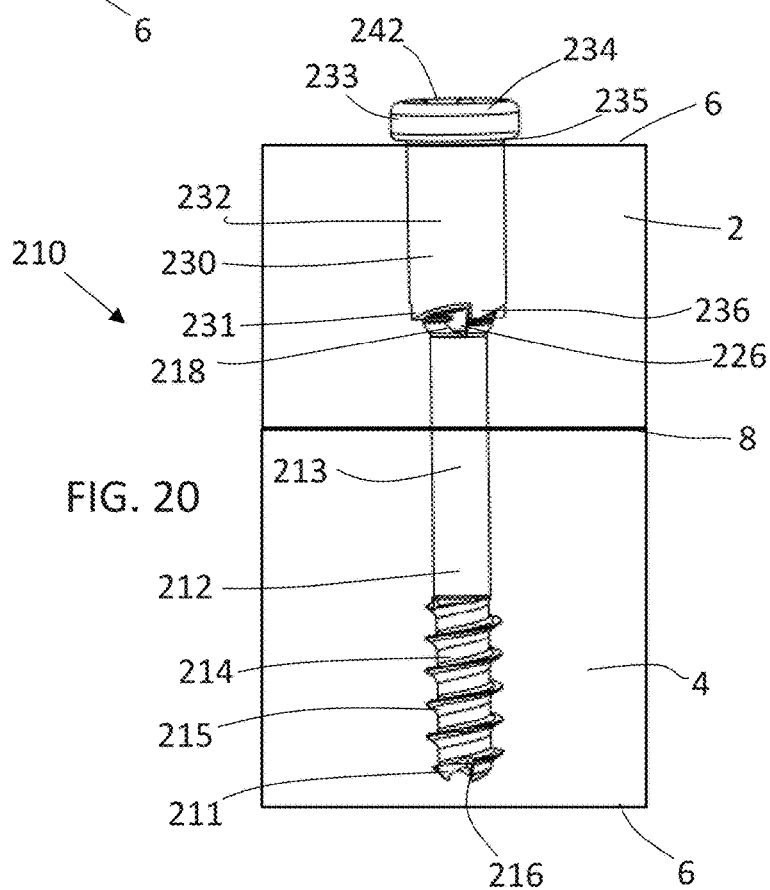
FIG. 20 is a plan view of the compression screw shown in FIG. 19 with the fracture reduced.

Turning now to FIGS. 19 and 20 an alternative version of a variable length compression screw 210 is shown. Compression screw 210 is similar to screw 10 and like elements will be labeled in a like manner. The compression screw 210 generally comprises two components: a bone screw 212 and a compression sleeve 230. The two component system is configured to be inserted at a fracture site as a single unit and may be easily removed from the fracture site as a single unit.

The bone screw 212 includes a shaft 214 extending from a distal end 211 to a proximal end, which may contain a drive feature (not visible in FIGS. 19 and 20). A series of bone engaging threads 215 extend radially from the shaft 214 at the distal end 211 and a series of sleeve engaging threads 218 extend radially from the shaft 214 at the proximal end. The distal end of the sleeve engaging threads 218 may include at least one cutting flute 226 configured to cut into the bone as the bone screw 212 is rotated. Any suitable type of thread for either thread series 215, 218 may be used to facilitate the function of the compression screw 210. A non-threaded section 213 may separate the threaded sections 215, 218. The shaft 214, including the non-threaded section 213 and the distal threaded section 214, may also have a reduced diameter relative to the proximal threaded section 218. The distal end 211 of the bone screw 212 may include at least one cutting flute 216 configured to cut into the bone as the bone screw 212 is rotated, for example, defining a self-drilling and/or self-tapping tip.

The compression sleeve 230 includes a hollow tubular body 232 extending from a distal end 231 to a proximal end 233 with an internal passage therethrough. The compression sleeve 230 includes a series of internal threads configured to engage the sleeve engaging threads 218 of the bone screw 212 such that the bone screw 212 and the compression sleeve 230 are threadably adjustable to one another. The proximal end 233 of the compression sleeve 230 defines a radially extending head 234 which defines a shoulder 235 between the tubular body 232 and the head 234. The shoulder 235 is configured to rest against cortical bone 6 of the bone segment 2. A drive feature 242 is defined in the head 234 of the compression sleeve 230 and is configured and dimensioned to be any shape (e.g., hexagonal, etc.) that corresponds with the end of the driving instrument designed to engage the compression sleeve 230. The distal end 231 of the compression sleeve 230 may be provided with one or more cutting flutes 236 configured to cut into the bone as the compression sleeve 230 is rotated.

The insertion of the variable length compression screw 210 at the bone fracture site allows for precise placement of the screw 210 because it does not require the tip of the bone screw 2112 to move for compression. In other words, the distal tip 211 may be at substantially the same position in bone portion 4 before and after compression of the fracture 8. The variable length compression screw 210 may be placed in its necessary position from the start, thereby allowing the surgeon to capitalize on the good bone farther away from the fracture line (e.g., close to or within cortical bone 6 in bone portion 4).

Traditional compression screws may achieve compression during insertion of the screw resulting in the surgeon estimating the length of the screw and depending on the estimated amount of compression that will be achieved during insertion. In this type of approach, initial positioning of the compression screw needs to accommodate the extra depth the screw will be inserted when achieving compression. The uncertainty in the amount of achievable compression results in uncertainty of the final position of the screw. Screw position is critical when trying to maximize bone purchase with the bone threads of the screw while preventing the bone threads from protruding into the articulating surface of adjacent bones causing disruption of the joint. Surgeon estimates, however, of the lengths of screws and achievable compression may result in not achieving the desired compression and/or the screw being too long or short. The variable length compression screw 210, on the other hand, allows for placement of the screw 210 independently from compression of the fracture 8.

As seen in FIG. 19, a first bone portion 2 is separated from a second bone portion 4, for example, by a fracture 8 having a gap therebetween. The compression screw 210 is inserted into the bone fragments 2, 4 as one compression screw 210 with two independently working parts: compression sleeve 230 and bone screw 212. The compression screw 210, in its entirety, may be inserted, for example, using a compression screw driver. The compression screw 210 can be placed at its final depth with compression achieved at the proximal end of the screw 210. Placement of the compression screw 210 at its final depth (before compression) allows the screw 210 to be placed in the optimal position, close to but not through the far cortical wall 6 in bone portion 4.

FIG. 20 shows compression screw 210 after compression with the fracture 8 reduced (bone portions 2, 4 almost or completely touching). The combination of the head 234 on the compression sleeve 230 and the threaded connection between the compression sleeve 230 and the bone screw 212 maximizes the ability to compress the bone fragments 2, 4. The head 234 is able to buttress against the cortical wall 6 of the bone 2 while the threaded connection between the bone screw 212 and the compression sleeve 230 pull the bone fragments together.

Historically, compression may be achieved in one of two ways: 1) screw driver controlled and 2) implant controlled. Screw driver controlled compression is typically done by attaching the screw driver directly to a threaded head (commonly referred to as headless because of the threads on screw) of the screw covering the threads on the head. Covering the threads on the head of the screw creates a buttress between the driver and the bone. The screw is inserted into the bone pulling the driver against the near cortical wall to achieve compression. Once the desired compression is achieved, the threaded head of the screw is released and the screw is inserted to final depth. Since the driver creates the buttress for compression, compression can be lost when releasing the driver from the threaded head. Additionally, the threads on the head of the screw are inserted into the bone flush or subflush to the near cortical wall. The cortical wall can provide a good buttress for the screw to maintain its compression due to the high density of the cortical wall. Screws that are inserted below the cortical wall rely on the thread purchase of the threaded head in the cancellous bone, which is typically a softer less dense bone than cortical bone.

Implant controlled compression addresses the complications of relying on the driver for compression but does not solve the complications of screw positioning. Other systems may use a two-part screw with a threaded head and main screw. The threaded head of the screw is placed at or below the cortical wall, relying on the threaded head to maintain position in the cancellous bone. Compression is achieved by unlocking the screw driver so the main screw can be threaded deeper into the bone to achieve compression. Achieving final compression by inserting the main screw deeper into the bone can result in the screw protruding out of the articulating surface causing disruption in the joint. Complications can also arise from relying on the main screw achieving compression from screw purchase in pore quality bone. Since the main screw is not fully inserted before compression, the main screws threads may lie within the fractured bone relying on the strength of the fractured bone to achieve compression. Thus, screw driver controlled and implant controlled compression can result in a loss of compression when releasing the threaded head from the driver and the main screw advancing out of the bone, respectively.

The variable length compression screw 210 described herein may enhance screw placement, provide optimal compression, and result in the utilization of good cortical bone 6 for buttressing. The variable length compression screw 210 may be inserted into the bone 2, 4 as one, single unit. After the bone screw 212 is inserted into the bone at full depth, near but not into the far cortical wall 6, the bone fragments 2, 4 can be compressed by the compression sleeve 230. The compression sleeve 230 has a non-threaded head 234 that creates a buttress between the head 234 and the cortical wall 6 allowing the screw 210 to compress the fracture 8. The distance to distal tip 211 is substantially the same before compression (FIG. 19) and after compression (FIG. 20), thereby allowing for predictable and optimal placement. The compression sleeve 230 and bone screw 212 compress the fracture by the threaded connection between them. The mechanical connection between the compression sleeve 230 and the bone screw 212 is a reliable controlled mechanical feature. The variable length compression screw 210 achieves compression from compression sleeve 230 on the bone screw 212 and does not rely on a threaded head or driver compression.

The variable length compression screw 210 may also be easily removed, if desired. Removal of a two-piece compression screw, historically, requires a screw driver to engage with the drive feature of the bone screw 212. Bone ingrowth inside of the head may prevent a driver from inserting through the head and into the main screw in order to back out the screw. This bone ingrowth must be removed before the driver can engage with the screw. The variable length compression screw 210 minimizes the amount of bone ingrowth removal necessary to remove the variable length compression screw 210. This is accomplished by swaging the proximal end of the bone screw 212 after the compression sleeve 230 is threaded onto the bone screw 212, preventing separation of the bone screw 212 and compression sleeve 230. The inability to separate the compression sleeve 230 from the bone screw 212 allows the variable length compression screw 210 to be removed by only the compression sleeve 230.

Swaging the proximal end of the screw 210 is the deforming of material on the screw to prevent the separation of the compression sleeve 230 from the bone screw 212. By coupling the compression sleeve 230 and the bone screw 212 together, removal of the variable length compression screw 210 occurs simply by backing out the compression sleeve 230. The swaging helps to minimizes the amount of bone ingrowth removal necessary to remove the variable length compression screw 210.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A method for applying compression between a first bone portion and a second bone portion having a gap therebetween, the method comprising:

providing a compression screw having an outer sleeve and an inner bone screw, the outer sleeve having a non-threaded head which defines a radially extending shoulder, the inner bone screw having a proximal threaded portion being threadedly engaged with the outer sleeve, wherein a distal end of the proximal threaded portion has at least one cutting flute configured to cut into the first bone portion as the inner bone screw is rotated, and wherein the inner bone screw includes a distal threaded portion and a non-threaded portion between the distal threaded portion and the proximal threaded portion;

inserting the compression screw in the first bone portion and the second bone portion as a single unit until a distal end of the inner bone screw reaches a final location in the second bone and such that the cutting flute on the proximal threaded portion cuts the first bone as the proximal threaded portion becomes positioned within the first bone portion;

rotating the inserted outer sleeve to move the outer sleeve toward the inner bone screw while the distal end of the inner bone screw remains at the same final location such that the radially extending shoulder of the outer sleeve contacts an outer surface of the first bone and compresses the first bone towards the second bone, wherein the final location of the distal end of the inner bone screw remains the same before and after the compression.

2. The method of claim 1, further comprising rotating the outer sleeve to remove the inserted outer sleeve and inner bone screw without engaging any drive feature of the inner bone screw, wherein a proximal portion of the inner bone screw is deformed to prevent the outer sleeve from disengaging from the inner bone screw during the removal.

3. The method of claim 2, wherein the proximal end of the inner bone screw is swaged to prevent the outer sleeve from disengaging from the inner bone screw.

4. The method of claim 1, wherein the outer sleeve is positioned within the first bone portion and the inner bone screw is positioned within the first bone portion, the second bone portion, and across the gap.

5. The method of claim 4, wherein the distal threaded portion is positioned within the second bone portion, and the non-threaded portion is positioned across the gap.

6. The method of claim 4, wherein the non-threaded portion has a reduced diameter relative to the proximal threaded portion.

7. The method of claim 4, wherein the the distal threaded portion includes a cutting flute.

8. The method of claim 1, wherein the outer sleeve has a plurality of cutting flutes configured to cut into the first bone portion.

9. The method of claim 1, wherein the gap is a fracture.

10. A method for applying compression between a first bone portion and a second bone portion having a gap therebetween, the method comprising:

providing a compression screw having an outer sleeve and an inner bone screw, the outer sleeve having a non-threaded head which defines a radially extending shoulder, the inner bone screw having a proximal threaded portion being threadedly engaged with the outer sleeve, wherein a distal end of the proximal threaded portion has at least one cutting flute configured to cut into the first bone portion as the inner bone screw is rotated, wherein a distal end of the proximal threaded portion has at least one cutting flute configured to cut into the first bone portion as the inner bone screw is rotated, and wherein the inner bone screw includes a distal threaded portion and a non-threaded portion between the distal threaded portion and the proximal threaded portion;

inserting the compression screw in the first bone portion and the second bone portion as a single unit until a distal end of the inner bone screw reaches a final location in the second bone and such that the cutting flute on the proximal threaded portion cuts the first bone as the proximal threaded portion becomes positioned within the first bone portion;

rotating the inserted outer sleeve to move the outer sleeve toward the inner bone screw while the distal end of the inner bone screw remains at the same final location such that the radially extending shoulder of the outer sleeve contacts an outer surface of the first bone and compresses the first bone towards the second bone, wherein the final location of the distal end of the inner bone screw remains the same before and after the compression; and removing the compression screw by the outer sleeve without engaging any drive feature of the inner bone, wherein a proximal portion of the inner bone screw is deformed to prevent the outer sleeve from disengaging from the inner bone screw during the removal.

11. The method of claim 10, wherein the distal threaded portion is positioned within the second bone portion, and the non-threaded portion is positioned across the gap.

12. The method of claim 10, wherein the non-threaded portion has a reduced diameter relative to the proximal threaded portion.

13. The method of claim 10, wherein the distal threaded portion includes a cutting flute.

14. The method of claim 10, wherein the outer sleeve has a plurality of cutting flutes configured to cut into the first bone portion.

15. The method of claim 10, wherein the proximal portion of the inner bone screw is swaged to prevent the outer sleeve from disengaging from the inner bone screw.

\* \* \* \* \*